United States Patent
Stroïazzo Mougin (10) Patent No.: US 9,637,760 B2
(45) Date of Patent: May 2, 2017

(54) PROCESS FOR PRODUCING A BIOCRUDE EMPLOYING MICROALGAE

(76) Inventor: Bernard A. J. Stroïazzo Mougin, Alicante (ES)

( * ) Notice: Subject to any disclaimer, the term of this patent is extended or adjusted under 35 U.S.C. 154(b) by 659 days.

(21) Appl. No.: 13/805,368

(22) PCT Filed: Jun. 23, 2010

(86) PCT No.: PCT/ES2010/070423
§ 371 (c)(1),
(2), (4) Date: Mar. 1, 2013

(87) PCT Pub. No.: WO2011/161273
PCT Pub. Date: Dec. 29, 2011

(65) Prior Publication Data
US 2013/0199083 A1    Aug. 8, 2013

(51) Int. Cl.

| | |
|---|---|
| C10L 1/00 | (2006.01) |
| C12P 5/02 | (2006.01) |
| C12N 1/12 | (2006.01) |
| C12P 39/00 | (2006.01) |
| C10G 1/02 | (2006.01) |
| C12P 1/00 | (2006.01) |

(52) U.S. Cl.
CPC .................. *C12P 5/02* (2013.01); *C10G 1/02* (2013.01); *C10L 1/00* (2013.01); *C12N 1/12* (2013.01); *C12P 1/00* (2013.01); *C12P 5/023* (2013.01); *C12P 39/00* (2013.01); *C10G 2300/1014* (2013.01); *Y02E 50/343* (2013.01); *Y02P 30/10* (2015.11); *Y02P 30/20* (2015.11)

(58) Field of Classification Search
CPC ..... C10L 1/00; C10L 5/40; C12N 1/12; C12P 1/04; C12P 39/00; C12P 5/02; C12P 1/00; C12P 5/023; Y02E 50/343; C10G 1/02; C10G 2300/1014; Y02P 30/10; Y02P 30/20
USPC .............................................. 44/307; 435/167
See application file for complete search history.

(56) References Cited

U.S. PATENT DOCUMENTS

| | | | | |
|---|---|---|---|---|
| 4,354,936 A | * | 10/1982 | Ishida ....................... | C02F 3/28 210/170.01 |
| 5,541,056 A | * | 7/1996 | Huntley ................. | C12M 21/02 435/257.1 |
| 2006/0151402 A1 | * | 7/2006 | Hsu ......................... | C02F 1/66 210/764 |
| 2009/0126265 A1 | * | 5/2009 | Rasmussen ............ | A01G 33/00 47/1.4 |
| 2010/0015677 A1 | * | 1/2010 | Iversen .................... | C12P 5/02 435/161 |

(Continued)

OTHER PUBLICATIONS

Amin S. Review on biofuel oil and gas production processes from microalgae. Energy Conversion and Management 2009;50:1834-1840.*

*Primary Examiner* — Latosha Hines
(74) *Attorney, Agent, or Firm* — Ladas & Parry LLP (57) ABSTRACT

This invention refers to a procedure for obtaining a biocrude from greenhouse gases, a procedure which is advantageous industrially and continuous. By means of said procedure it is possible to capture, convert and revalue $CO_2$, among other greenhouse gases, in an efficient manner, in such a way that a net negative balance is obtained, which in other words means that with this procedure it is possible to capture more $CO_2$ than is generated which makes it beneficial and sustainable in the environment.

24 Claims, 3 Drawing Sheets

(56) References Cited

U.S. PATENT DOCUMENTS

2010/0267122 A1* 10/2010 Chinnasamy ............ C12N 1/12
435/257.3

* cited by examiner

PROCESS FOR PRODUCING A BIOCRUDE EMPLOYING MICROALGAE

RELATED APPLICATION INFORMATION

This application is a 371 of International Application PCT/EP2010/070423 filed 23 Jun. 2010 Entitled "PROCESS FOR PRODUCING A BIOCRUDE EMPLOYING MICROALGAE", which was published on 29 Dec. 2011, with International Publication Number WO 2011/161273 A1.

TECHNICAL FIELD

This invention refers to a procedure for obtaining a biocrude from green house gases in a procedure which is industrially advantageous and carried out continuously. Through the procedure it is possible to capture, convert and reevaluate $CO_2$, as well as other greenhouse gases ($NO_x$, $CH_4$ . . . ) in an efficient manner and in such a way that a negative net balance is achieved, or in other words this procedure enables more $CO_2$ to be captured than that which is generated, which is both beneficial and sustainable for the environment.

In this way a high energy density biocrude is obtained, suitable for use in any combustion engine, turbine or boiler. This biocrude is mainly characterised by its similarity to current fuels (amalgam of chemical components, hydrocarbons, which following a refining stage result in different types of refined fuel such as petrol, diesel, kerosene etc.).

Furthermore this invention refers to the use of biocrude in combustion engines.

STATE OF THE ART

Global warming refers to the increase of average temperatures of the earth's atmosphere and that of the oceans which is causing climate change. This increase has been exacerbated in the latter decades of the 20th century and the early 21st century as a result of human activity, which to some extent, as a result of industrial emissions (emissions of greenhouses gases such as $NO_x$, $CO_2$, $CH_4$ etc) along with felling of forests has upset the existing balance in nature. This phenomenon is known as the greenhouse effect.

Greenhouse gases absorb infrared photons emitted by the ground heated by the sun. The energy of those photons is not sufficient to cause chemical reactions, in order to break covalent bonds, but rather they simply increase the energy of rotation and vibration of the molecules involved. Excess energy is then transferred to other molecules through molecular collision in the form of kinetic energy, that is, as heat, increasing air temperature. In the same way, the atmosphere cools, emitting infrared energy when the corresponding transitions from vibrational and rotational state in the molecules are introduced to lower levels of energy. All those transitions require changes in the dipole moment of the molecules (that is, modifications in the separation of electrical charges in their polar bonds) which leaves out the two main gases of which air is composed namely, nitrogen ($N_2$) and oxygen, the molecules of which, since they are formed by two equal atoms, lack any dipole moment.

The "anthropogenic theory" predicts that global warming will continue if greenhouse gases gases continue to be emitted. The human race today is one of the most important climatic agents. Its influence began with deforestation of forests for planting crops or r pasture land however, at the present time human influence has greatly increased due to the production of abundant gas emissions which cause the greenhouse effect, that is, $CO_2$ from factories and transport vehicles and methane from intensive livestock farming and paddy fields.

Currently both gas emissions and deforestation have increased to such an extent that their reduction would appear difficult in the short and mid term due to the technical and economic implications of the activities involved.

By the end of the 17th century man began to use fossil fuels accumulated by the Earth in its subsoil throughout its geological history. Burning oil, carbon and natural gas has led to an increase in $CO_2$ in the atmosphere which has recently risen to 1.4 ppm per year and produces the resulting increase in temperature. It is considered that since man began to measure temperature about 150 years ago (in the industrial era) it has risen by 0.5° C. and it is estimated that there will be a 1° C. increase by 2020 and 2° C. by 2050.

There are several potential effects of global warming which, according to global warming theories, will hypothetically affect the environment and human life. The main effect is the progressive increase in average temperatures. This in turn leads to a number of changes such as the increase in sea levels, alterations to agricultural ecosystems, expansion of tropical diseases, and increase in the intensity of natural phenomena. Some of these phenomena are actually occurring at the present time, however, it is difficult to specify any direct link with global warming.

For this reason the Kyoto Protocol I promoted a reduction of contaminating emissions such as greenhouse gases (mainly $CO_2$).

Similarly, due to the fact that one of the main sources of $CO_2$ emissions is oil combustion and its derivates, various systems and procedures have been developed to minimise this problem.

One of these is the development of biocrudes (biodiesel) based on extensive cultivation of superior crops, however to date they have demonstrated their low effectiveness; furthermore, in order to be able to generate a significant amount of biocrudes, extensive areas of terrain are required; often growing these crops requires the previous felling of existing forests and in many cases these are also burned with the concomitant emissions this entails.

Subsequently research groups developed new systems and procedures which make use of microalgae as agents for capturing $CO_2$, in order to subsequently transform them to biocrudes (biodiesel), through reactors open to the outside, which had a considerable disadvantage due to the pollution created by the growing methods (in addition they are more difficult to control, they cannot evacuate $O_2$, less production per ha etc.).

Due to this considerable problem, closed systems were designed which worked horizontally, and thus possible external contamination was eliminated. However, the main problem with these was that, since the systems are horizontal and work with extensive crop areas, moving them or treating them requires a considerable contribution of energy to the system which, in short, generated extensive pollutant emissions and unfavourable energy balances.

Subsequently and up to the present, procedures are being developed to remedy all the aforementioned problems and generate biocrudes. (Biodiesel). However, these still assume an unfavourable net balance as ultimately they continue to emit enormous amounts of $CO_2$ to the atmosphere.

The systems described to date are systems which, with their limitations, really can provide biocrudes (in this case biodiesel) based on the capture of CO2. Nevertheless, due to the low yield per hectare, production per m³ (and therefore worse ratios of $CO_2$ capture), the complexity of the operation and production capacity for only one fuel (since it only provides biodiesel it does not resolve the scarcity of oil in future) there are a number of reasons for seeking a new means of resolving all these points, and specifically a means which will capture greater amounts of $CO_2$ than that which is subsequently emitted, or in other words, new sustainable procedures are required which will achieve a negative net balance of $CO_2$ to the atmosphere.

DESCRIPTION OF THE INVENTION

This invention refers to a procedure for obtaining a biocrude from greenhouse gases which is both advantageously industrial and continuous. Through this procedure it is possible to capture, convert and reevaluate $CO_2$ among other greenhouse gases ($NO_x$, $CH_4$ . . . ) in an efficient manner, in such a way that a negative net balance is achieved or, in other words, through this procedure more $CO_2$ is captured than is generated, which is both beneficial and sustainable for the environment.

In this way a high density energy biocrude is obtained appropriate for use directly in any combustion engine, turbine or boiler which functions using fuel-oil. This biocrude is mainly characterised by its similarity to currently used crude oils (amalgam of chemical components, hydrocarbons which following a refining process obtain different types of fuel, petrol, diesel, kerosene etc.)

Therefore, a first aspect of the invention refers to a procedure for obtaining a biocrude based on a gas which comprises $CO_2$, a procedure which includes the stages of:
  a. Supply of the gas comprising $CO_2$ to a reactor containing a culture which includes at least one species of microalga able to carry out photosynthesis;
  b. Photosynthesis process carried out by the microalga species based on $CO_2$ supplied to produce a biomass;
  c. Anaerobic fermentation of the biomass obtained;
  d. Thermo-chemical decomposition of the fermented biomass at a pressure between 0 and 20 MPa and at a temperature between 200 and 420° C. in order to obtain a biocrude mixed with water and gases, and
  e. Separation of biocrude obtained,
characterised in that following the stage of carrying out photosynthesis, between 5% and 100% of the culture is released from the reactor which is subsequently separated into a solid fraction which contains biomass, which will subsequently be subjected to anaerobic fermentation stage and a liquid fraction which contains carbonates and/or bicarbonates which are separated from the liquid part, in order to subsequently return the liquid fraction to the reactor at least partially, and substantially free from carbonates and/or bicarbonates.

In a general manner, the invention procedure comprises the stages of:
  biological treatment of greenhouse gases;
  mechanical treatment of the culture medium;
  mechanical-chemical treatment of the aqueous phases; and
  mechanical-chemical treatment of the biomass;
Stage of Biological Treatment of Greenhouse Gases:
According to a preferred first embodiment, the stage of biological treatment of greenhouse gases comprises the following sub-phases:
  supply of a gas which includes $CO_2$ to a reactor which contains a culture comprising at least one species of micro-alga which is able to produce photosynthesis; and
  capture and biological conversion of $CO_2$ through the photosynthesis carried out by the micro-alga species in order to produce a biomass.

According to another preferred embodiment, the sub phase of supply of a gas containing $CO_2$ such as, for example, greenhouse gases, comprises an endogenous and/or exogenous supply of greenhouse gases to a photosynthetic type reactor in which at least one species of micro-alga able to carry out photosynthesis, is present.

In this respect throughout this descriptive report "greenhouse gases" shall be considered to be any gas which includes $CO_2$ and potentially other components such as NOx, $CH_4$ or others, in any combination. Nevertheless, it is only really necessary for the invention procedure that the gas includes at least $CO_2$. In this way these gases which are so harmful to the environment become part of the nutrients added to the reactor in order to "feed" the microalgae present therein.

Furthermore, the greenhouse gases added in an exogenous manner normally come from the atmosphere or any industry and the endogenous additives come from gases created in the procedure developed by this invention.

Based on the composition of these gases, a possible option is to subject them to a previous treatment prior to being introduced.

According to another preferred embodiment, an optional pre-treatment of greenhouse gases may be carried out by eliminating $SO_x$, $NO_x$, and humidity and by adapting the temperature to approximately 30-40° C. Having carried out the pre-treatment phase (if appropriate) these gases are introduced to the culture.

According to another preferred embodiment, the sub-phase of capture and biological conversion of $CO_2$ comprises the process of photosynthesis carried out by the microalgae. Furthermore, in the most preferred embodiments of the invention the reactor containing them is subjected to continuous exposure to light, albeit natural or artificial and to add to the culture medium both nutrients and optionally antibiotics and fungicides.

In this way, microalgae present in the reactor, due to the supply of a gas which includes at least $CO_2$, capture the carbon in the carbon dioxide and other nutrients, and they assimilate it and transform it to biological molecules of interest such as carbohydrates, fats and proteins.

Furthermore, in order for the microalgae to capture the greenhouse effect gases from the previous stage, the culture medium in the reactor is advantageously subjected to a turbulent regime. In this way it is ensured that the entire microalgae culture is able to capture said gases and obtain the light required to carry out photosynthesis. In addition, generating a turbulent medium provides the advantage of preventing the formation of fouling, that is, the undesirable accumulation of micro-organisms on the surface of the photo bioreactors. This creation of turbulence may be carried out by any means in order to achieve this purpose, although in preferred embodiments of the invention this is carried out by blowing into the reactor either air, N2, $CO_2$, CO, $NO_x$, and gases resulting from combustion or any combination thereof.

In addition, the microalgae present in the reactor are selected from the group formed by: Chlorophyceae, Bacillariophyceae, Dinophyceae, Cryptophyceae, Chrysophyceae, Haptophyceae, Prasinophyceae, Raphidophyceae, Eustigmatophyceae, or any combination of these.

Mechanical Treatment Stage of the Culture Medium

According to another preferred embodiment, the mechanical treatment stage of the culture medium comprises the sub-phases of:
- at least partial emptying or removal of the culture in the reactor;
- separating out the removed culture in a solid fraction containing biomass and a liquid fraction containing carbonates and/or biocarbonates;

According to another preferred embodiment, in the emptying sub-phase at least between 5 and 100% of the culture medium is removed, preferably between 5 and 50% and preferably even more, ie of the 10% of the culture medium, in such a way that the remainder is kept in the reactor and continues to capture and convert $CO_2$ in a continuous manner by means of the microalgae as a biological medium for performing this purpose. It is important to highlight the fact that this extraction % is replaced, preferably rapidly with water which is substantially lacking in algae and without carbonates or with a very low concentration of these, proceeding from separation stages which will be detailed below; the amount of algae present in the water which is re-added will depend on the efficacy of separation of each specific method.

According to another preferred embodiment, the sub-phase of separating the culture removed in a solid fraction which contains biomass and a liquid fraction which contains carbonates and/or bicarbonates, at least, one stage of mechanical extraction selected from filtration, centrifugation, flocculation, electro coagulation, ultrasound, evaporation, decantation or any combination thereof. In this way it is possible to separate the aqueous phase from the biomass.

According to another optional preferred embodiment, following the emptying stage, a stage of acidification of the culture or medium removed or extracted from the reactor will be carried out. In this optional sub-stage, the removed or extracted culture medium is accumulated in an accumulation tank, in which at least one acidifying agent is added until it reaches a pH of between 3.5 and 8, preferably between 6 and 8. The acidifying agent is selected from the group formed by $CO_2$ (this $CO_2$ may be bottled or industrial), mixture of $CO_2$ and air, strong or weak acids or any other combination thereof. Preferably the acidifying agent is a mixture of $CO_2$ with air. In this way it is possible to ensure that the medium from the reactor, which is rich in CO2 and bicarbonate, does not precipitate, (through non-formation of carbonates) and thus phenomena such as adherence and fouling are prevented.

Mechano-Chemical Treatment of the Aqueous Phase:

According to another preferred embodiment, the chemical treatment stage of the aqueous phase includes the following sub-phases:
- chemical conversion of $CO_2$ which is present in the liquid fraction resulting from at least partial removal of the culture from the reactor in the form of carbonates and/or bicarbonates in dissolution, in their corresponding carbonated forms precipitated through the addition of an alkali and
- at least partial recirculation of the liquid phase already substantially devoid of carbonates and/or bicarbonates in solution in the reactor.

Therefore, according to another preferred embodiment, the sub-phase of chemical conversion of $CO_2$ includes transporting the water resulting from the biomass separation from the water sub-phase to a clarification tank in which the aqueous phase is accumulated, comprising water, dissolved nutrients, $CO_2$, carbonate and bicarbonate all of which are dissolved. When the aqueous phase reaches the clarification tank, at least one basic medium is added in order to cause precipitation in the form of carbonates of the species which are in balance ($CO_2$, bicarbonate and carbonate). Therefore, in this way it is possible to eliminate even more $CO_2$, as it is transformed into carbonated salts which are useful in various industries and it is no longer a pollutant.

Once the water is free of $CO_2$, precipitated in the form of carbonate and bicarbonate, the sub phase or recirculation of water to the reactor is carried out where the culture medium is present.

In this way, at this point of the procedure, a dual elimination or conversion of $CO_2$ has been carried out; the capture or biological fixation carried out by the micro algae present in the culture medium, and a chemical conversion or transformation as a result of this precipitation. By doing this, there is less CO2, bicarbonate and carbonate in the culture water and it is able to capture further CO2 up to the limit of solubility. During the following cycle, the procedure is repeated and ends with the precipitation of most of this $CO_2$ which has been introduced. If this forced precipitation is not carried out, much of the $CO_2$ will remain dissolved in the aqueous phase which is returned by the culture. Therefore, when introducing the $CO_2$ into the culture once more, the capacity for dissolution will be less, as it already contains dissolved $CO_2$.

Mechano-Chemical Treatment Stage of the Biomass:

According to another preferred embodiment, the mechano-chemical treatment stage comprises the following sub-phases:
- anaerobic fermentation of the biomass obtained in the photosynthesis carried out by the microalgae;
- separation of the fermented biomass from the culture water;
- thermo-chemical transformation of the fermented biomass through thermo-chemical decomposition at a temperature between 200 and 420° C. and a pressure between 0 and 20 MPa in order to obtain a biocrude mixed with water and gases, and
- separation of biocrude obtained.

According to another preferred embodiment, the biomass from the sub-phase of separation from the biomass of the aqueous phases is subject to a sub-phase of anaerobic fermentation which takes place in a fermenter. During that fermentation at a temperature of between 10 and 165° C. and preferably between 30 and 75° C., the biomass is introduced with a solids concentration varying between 1 to 50% of solids, and preferably between 5 and 12%.

During the anaerobic fermentation, the biomass is transformed by different microbial communities present in the fermenter (anaerobic bacteria) losing O and N in the form of $H_2O$, $CO_2$ and $NH_3$ and becoming enriched in H and C. The product obtained following this stage is similar to kerogen (a precursor of petroleum). Together with the anaerobic fermentation, a process of metagenesis occurs, giving rise to the formation of methane, as a result of the fragmentation of the chains; this methane will be used as a source of heat energy.

According to another optional preferred embodiment, prior to the sub-phase of anaerobic fermentation, the biomass passes through a stage of homogenisation or cavitation in which the algae are subject to pressure of between 1 bar and 2500 bars, and preferably between 250-1200 bars, in order to produce their fragmentation. According to a preferred embodiment, the phase of homogenisation or cavitation is repeated between 1 to 5 times, preferably once. Subsequently, following the sub-phase of anaerobic fermentation, the resulting product is passed through a sub phase of separation of the fermented biomass from water by means of a process selected from filtration, centrifugation, flocculation, electro coagulation, ultrasound, evaporation, decantation or any combination of these. In accordance with this treatment, a biomass is obtained with a concentration of solids between 14-40% in solids, preferably between 20-25%.

Following the phase of separation of the fermented biomass from the water, a thermo chemical transformation stage will be carried out in which the biomass is subjected to high pressures and temperatures which results in the generation of hydrocarbons.

This stage consists of a chemical decomposition of organic material, caused by moderate heating at high pressures or atmospheric pressure, although preferably at high pressures. The main advantage of working at high temperatures (in the order of 10-20 MPa or atmospheric pressure) and moderate temperatures (from between 200 and 420° C., preferably between 240 and 340° C.) is that the basic raw material does not need to be dried, thus it is possible to introduce the raw material to the thermo chemical reactor with a humidity of up to 95%, preferably between 80-60%, which has the clear advantage of obviating the need for drying (heat energy saving). In this phase a biocrude is obtained.

Finally, a sub phase is preferably carried out in which water accompanying the biocrude is eliminated, using at least one method selected from the group formed by decantation, flocculation, coalescence, centrifugation, evaporators, dryers or any combination thereof, and thus a biocrude is obtained which may be used in internal combustion engines, boilers or turbines which work with fuel oil which does not need to be refined.

Optionally, according to a preferred embodiment, following a sub-phase eliminating the water, the biocrude obtained is subjected to a sub phase of homogenisation or cavitation, in which the algae is subjected to a pressure between 1 bar and 2500 bar, preferably between 250-1200 bar in order to produce their fragmentation. According to a preferred embodiment, the homogenisation or cavitation phase is repeated from 1 to 5 times, preferably once. In this way the following occurs:

Breakage of long chains of hydrocarbons in order to obtain light hydrocarbons, increases the number of alkenes, raises the rate of ketane, reduces the temperature of crystallisation and reduces the amount of harmful emissions.

Mixture of two fluids which are inter-mixed (biocrude and water).

Optionally, according to another preferred embodiment, following the sub-phase of eliminating water or following the homogenisation phase, a sub phase refining the biocrude will be carried out. The refining stage shall be equivalent to the existing conventional refining existing in the refinery except that the content of sulphur and heavy metals is lower or non-existent.

Based on the established objective, that is, based on the parts it is wished to obtain (petrol, diesel, kerosene, plastics etc), the structure of the refinery may be different. Therefore, based on this the plant shall also include at least one of the following phases:

Atmospheric distillation (or topping),
Vacuum distillation
gas plant,
hydro treatment of naphtha,
catalytic reforming.
Hydrocracking FCC Fluid Catalytic Cracking,
Visbreaking,
Isomerisation,
Alkylation,
steam cracking,
Bitumen blowing,
Coking.

Finally, through the procedure described in this invention, it has passed from a concentration of C from the molecule $CO_2$ (27% of C) to the final product (65-95% in C, preferably between 75-90%).

A second aspect of this invention refers to a biocrude obtained through the previously described procedure the characteristics of which are indicated below:

TABLE 1

| | |
|---|---|
| Density (kg/m$^3$) | 800-1200 |
| Cinematic Viscosity (50° C.) (mm$^2$/s) | 2-100 |
| Inflammation point (° C.) | 35-200 |
| Ash content (% m/m) | 0-3 |
| PCI (MJ/kg) | 29-45 |
| Aluminium (mg/kg) | <1 |
| Silica (mg/kg) | <1 |
| Vanadium (mg/kg) | <1 |
| Sodium (mg/kg) | <1 |
| Calcium (mg/kg) | <1 |
| Magnesium (mg/kg) | <1 |
| Phosphorus(mg/kg) | <1 |

A third aspect of this invention refers to the direct use of the biocrude obtained in internal combustion engines, turbines or boilers working with fuel oil.

A fourth aspect of the invention refers to the use of a gas which includes $CO_2$, such as the gas from cement industries for obtaining a biocrude using the procedure in this invention.

Throughout the description and the claims, the word "comprise" and its variants do not intend to exclude other technical characteristics, additives, components or steps. For experts in the art, other objects, advantages and characteristics of the invention shall be divulged partly from the description and in part from the practice of the invention. The following examples and figures are provided by way of illustration and are not intended to restrict the scope of the invention.

EXAMPLES OF AN EMBODIMENT

Below, a series of examples are given which at any given moment illustrate the synthesis of some specific components of this invention and in order to provide examples of the general procedures. In accordance with the foregoing, the following examples are not intended in any way to restrict the scope of the invention considered in this descriptive report.

In this descriptive report the symbols and conventions used in these procedures, diagrams and examples are consistent with those used in the International System and contemporary scientific literature, for example the Journal of Medicinal Chemistry. Unless indicated to the contrary all the basic materials were obtained from suppliers and were used without any additional purification. Specifically, it is possible to use the following abbreviations throughout this descriptive report: g (grams); mg (milligrams); kg (kilograms); μg (micrograms); L (liters); mL (milliliters); μL (micro liters); mmol (milimols); mol (mols); ° C. (degrees Celsius); Hz (hertz); MHz (megahertz); δ (chemical displacement) s (singlet); d (duplete); t (triplet); q (quadruplet); m (multiplet); NMR (nuclear magnetic resonance); M (molar); $Et_3N$ (triethylamine); DMF (dimethylformamide); DMSO (dimethylsulfoxide); ACN (acetonitryl); PBS (phosphate buffered saline); NCV (net calorific value).

Example n° 1: Energy Conversion of $CO_2$, Obtaining a Net Negative Balance

The point of departure in this procedure is the emission gases resulting from the combustion of a cement works and optionally the gases resulting from the combustion of the actual product obtained (from biocrude).

Below Table 2 shows an example of the gases emitted by the cement works:

TABLE 2

| | |
|---|---|
| Temperature | 420° C. |
| Pressure | 1 Bar |
| Density | 0.79 kg/m³ |
| Mass flow | 2,000 kg/h |
| Specific heat | 0.25 kcal/kg |
| Volumetric flow | 2,531.64 m³/h |
| $CO_2$ | 12% V |
| $N_2$ | 61% V |
| $O_2$ | 1.9% V |
| $H_2O$ | 20.7% V |
| $CH_4$ | 2,500 ppm |
| $NO_x$ | 90 ppm |
| $SO_2$ | 50 ppm |
| CO | 1.65 ppm |

In accordance with the composition of the cement works gas, it was considered that the only treatment to be carried out was the elimination of $SO_x$ and the reduction of temperature. For this purpose an absorption column was installed in countercurrent with NaOH (aqueous dissolution at 10% of NaOH). It is important to point out that in the invention procedure, in addition to the reduction in the net balance of $CO_2$, a reduction in the concentration of $NO_x$ is also obtained (95% NO and the remainder $NO_2$) in the end product as a result of the dissolution of water from the NO and $NO_2$ (particularly the latter). Following this treatment, a gas with the following composition (Table 3) is introduced.

TABLE 3

| | |
|---|---|
| Temperature | 40° C. |
| Pressure | 1.98 Bar |
| Density | 2.22 kg/m³ |
| Mass flow | 1,760 kg/h |
| Specific heat | 0.24 kcal/kg |
| Volumetric flow | 792.79 m³/h |
| $CO_2$ | 13.5% V |

TABLE 3-continued

| | |
|---|---|
| $N_2$ | 63% V |
| $O_2$ | 2.1% V |
| $H_2O$ | 3.2% V |
| $CH_4$ | 2,300 ppm |
| $NO_x$ | 62 ppm |
| $SO_2$ | 2 ppm |
| CO | 0 ppm |

In addition to the gases resulting from the cement work emissions, as mentioned previously once again the gases resulting from combustion of the biocrude obtained in the process are reintroduced to the culture; below the composition of the this gas is presented at the outlet of the treatment system, (using scrubber only for tempering in this case there is no $SO_x$ and therefore NaOH is not introduced):

TABLE 4

| | |
|---|---|
| Temperature | 40° C. |
| Pressure | 1.98 Bar |
| Mass flow $CO_2$ | 78 kg/h |
| $CO_2$ | 14.9% V |
| $N_2$ | 58% V |
| $O_2$ | 2.7% V |
| $H_2O$ | 1.1% V |
| $CH_4$ | 1,100 Ppm |
| $NO_x$ | 120 Ppm |
| $SO_2$ | 0 Ppm |
| CO | 0 ppm |

Figure 1:
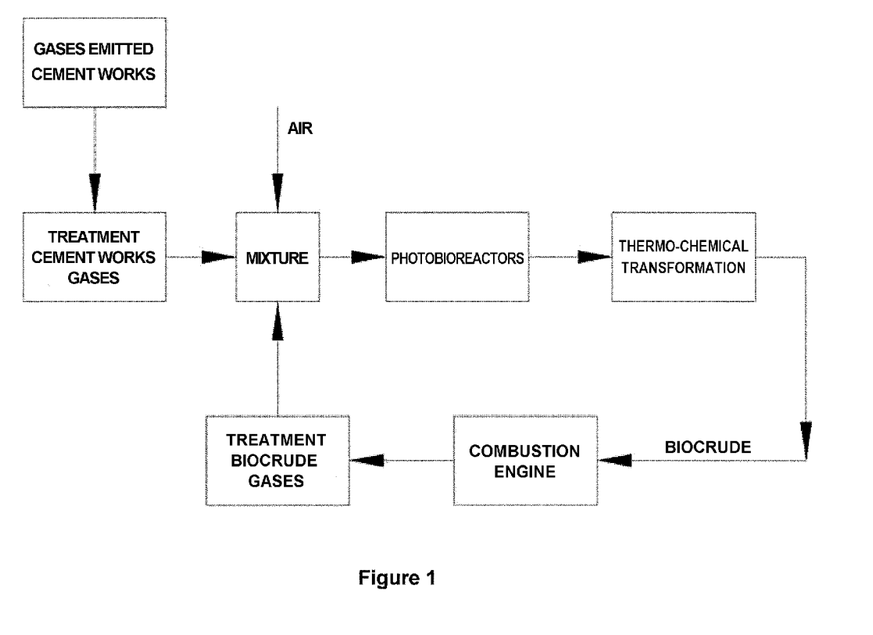
FIG. 1—shows a block diagram of the procedure in the present invention. It illustrates each of the stages in the procedure.
Figure 2:
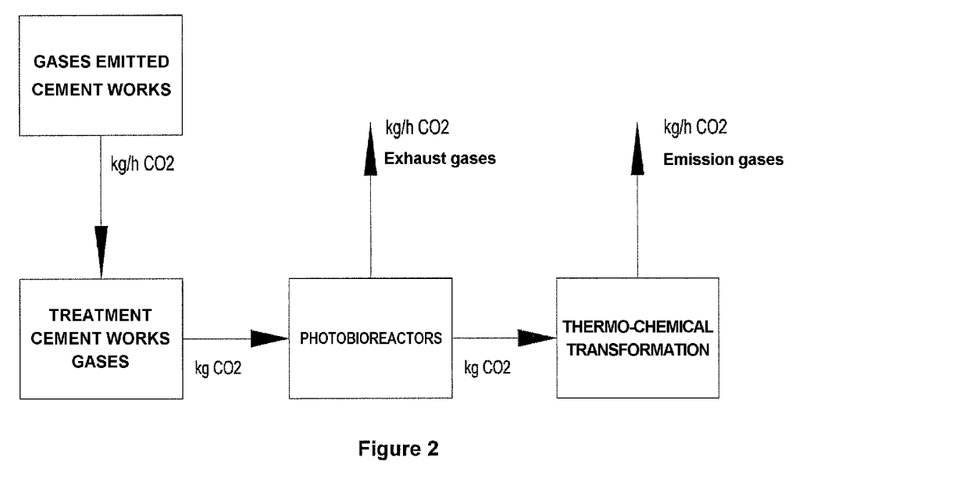
FIG. 2—shows a diagram representing the energy conversion of $CO_2$, in accordance with a net negative balance.

The general diagram is represented in FIG. 2. The gases are mixed in a tank designed for this specific purpose and system. In this mixing tank in addition to mixing these two currents a third air current is mixed to adapt the final mixture to the desired $CO_2$ concentration; in this specific case the average is 13.5% $CO_2$. In order to make the mixture, the concentration of $CO_2$ of the two first currents is measured and an electrovalve is activated to allow more or less air to pass through, thus regulating the final concentration. Therefore, this mixture is that which is introduced into the reactors (continuously agitated photosynthetic reactors which allow light to pass through and which are made of transparent material to this effect) which contain a monospecific culture of microalgae (Nannochloris sp).

In order to study the $CO_2$ taken up by the system, $CO_2$ composition is continuously measured at the entrance and outlet. According to this data it is possible to determine the amount of $CO_2$ captured by the system (biological fixation+ chemical fixation); together with the dry weight of the culture and it is possible to determine how much $CO_2$ has been biologically fixed by the alga depending on its photosynthetic behaviour) and how much has been fixed by the system. Below Table 5 shows the results of the $CO_2$ monitoring:

TABLE 5

| Time | t (min) | % $CO_2$ entry | X $CO_2$ entry (L $CO_2$/L gas) | GAS FLOW ENTRY (l/min) | % $CO_2$ outlet |
|---|---|---|---|---|---|
| 0:00:00 | 10 | 0 | 600 | 1.16 | −128.76 |
| 0:10:00 | 10 | 0 | 600 | 1.1 | −122.1 |
| 1:00:00 | 50 | 0 | 600 | 0.94 | −521.7 |
| 2:00:00 | 60 | 0 | 600 | 0.62 | −412.92 |
| 3:00:00 | 60 | 0 | 600 | 0.36 | −239.76 |
| 4:00:00 | 60 | 0 | 600 | 0.19 | −126.54 |
| 5:00:00 | 60 | 0 | 600 | 0.08 | −53.28 |
| 6:00:00 | 60 | 0 | 600 | 0 | 0 |

TABLE 5-continued

| Time | t (min) | % CO$_2$ entry | X CO$_2$ entry (L CO$_2$/L gas) | GAS FLOW ENTRY (l/min) | % CO$_2$ outlet |
|---|---|---|---|---|---|
| 7:00:00 | 60 | 0 | 600 | 0 | 0 |
| 8:00:00 | 60 | 0 | 600 | 0 | 0 |
| 9:00:00 | 60 | 13.49 | 600 | 0.13 | 8,897.76 |
| 10:00:00 | 60 | 13.51 | 600 | 1 | 8,331.66 |
| 11:00:00 | 60 | 13.51 | 600 | 2.25 | 7,499.16 |
| 12:00:00 | 60 | 13.51 | 600 | 3.2 | 6,866.46 |
| 13:00:00 | 60 | 13.5 | 600 | 3.69 | 6,533.46 |
| 14:00:00 | 60 | 13.5 | 600 | 3.86 | 6,420.24 |
| 15:00:00 | 60 | 13.5 | 600 | 3.89 | 6,400.26 |
| 16:00:00 | 60 | 13.5 | 600 | 3.87 | 6,413.58 |
| 17:00:00 | 60 | 13.5 | 600 | 3.89 | 6,400.26 |
| 18:00:00 | 60 | 13.52 | 600 | 4.2 | 6,207.12 |
| 19:00:00 | 60 | 13.5 | 600 | 5.1 | 5,594.4 |
| 20:00:00 | 60 | 0 | 600 | 4 | −2,664 |
| 21:00:00 | 60 | 0 | 600 | 2.2 | −1,465.2 |
| 22:00:00 | 60 | 0 | 600 | 1.45 | −965.7 |
| 23:00:00 | 60 | 0 | 600 | 1.3 | −865.8 |
| 23:50:00 | 50 | 0 | 600 | 1.18 | −654.9 |

In accordance with this Table, production will be 681.11 kg/per day of biocrude for a plant with a total volume of 735 m$^3$. In order to obtain this production based on the efficacy of CO$_2$ capture of 69%, calculated on the basis of the previous table, it will be necessary to supply the photobioreactors with 342.49 kg/h of CO$_2$; 264.44 kg of CO$_2$/h originating from the cement works and the remaining 78 kg CO$_2$/h resulting from feedback provided by the combustion emissions of the actual biocrude introduced.

In order to carry out the process of obtaining this biomass, firstly 367.64 m$^3$ per day is extracted (50% of the culture). Prior to passing to the following phase of centrifugation (1$^{st}$ extraction stage), it should pass through an acidification stage which takes place in a 500 m$^3$ tank. The basics of this acidification stage are as follows:

The culture extracted as a result of the continuous bubbling of exhaust gases has a content of CO$_2$, bicarbonate and carbonate in a high solution. When this CO$_2$ is left to bubble, the pH in the solution tends to rise, displacing the balance towards the formation of carbonates. If a lot of carbonate is formed it will exceed the point of solubility and this will begin to precipitate. This precipitation could cause a fouling problem and in turn the fouling could cause contamination and further complications in the decanting of water. Therefore as the mechanical separation (1$^{st}$ separation stage) is unable to process all the volume extracted at once, during this storage phase an acid needs to be added. Specifically in this case a solution of H$_2$SO$_4$ (1M) is added in order to keep the pH permanently below 7.5.

Having emptied 367.64 m$^3$ of culture, the mechanical separation of water from the biomass is effected. For this purpose centrifugation is used and in this way a volume of 1.89 m$^3$/per day is obtained at a concentration of 15% solids.

In addition to the concentrated fraction (15% solids), an aqueous fraction (permeated) is obtained, amounting to a total volume of 3,657 m$^3$/per day. This water, due to the fact that it formed part of the culture, is charged with CO$_2$, bicarbonate and carbonate. In order to release this charge from the water it is made alkaline with NaOH until it reaches a pH 9 in order to displace the balance towards the formation of carbonate, and in this way it exceeds the limit of solubility of the carbonate and causes it to precipitate. Thus CO$_2$, is chemically captured obtaining water poor in CO$_2$, bicarbonate and carbonate. This water which is poor in these elements is introduced into the system once more (to the photobioreactors) with a renewed capturing capacity in terms of CO$_2$. If this water were to be introduced without carrying out a previous stage of chemical capture, the CO$_2$ assimilation capacity of the water would be minimal as it would be close to saturation.

The concentrate with 15% solids resulting from centrifugation, passes to a stage of anaerobic fermentation at 38° C. During anaerobic fermentation the biomass is transformed by the various microbial communities present (anaerobic bacteria) losing O and N in the form of H$_2$O, CO$_2$ and NH$_3$ and becoming enriched in H and C. As the fermentation process progresses, it is noted how the N and O drops as the H and C content rises. At the same time methane is generated as a consequence of the fragmentation of these molecules, providing energy which is used as a source of thermal energy for the following thermochemical stage. In accordance with the fragmentation of the 54.57 kg/h of dry biomass which could potentially pass to the second stage, only 45.48 kg/per day passes to the following stage as a result of the fragmentation and decomposition.

Subsequently following the anaerobic fermentation stage the resulting product is subjected to centrifugation once more, this time until 23% solids are obtained; this product, produced at a production rate of 967 kg/per day, despite its pasty texture can nevertheless be pumped and it is passed to the following thermochemical transformation stage. The clearer water resulting from this process, (1.6 m$^3$/per day), is charged with ammonia, and is returned once more to the photobioreactors, with the ammonia serving as a further contribution of nutrients to the micro-organisms.

The thermo-chemical transformation takes place in a reactor at 270° C. and 22 MPa in a continuous process supplied at a rate of 40.32 kg/h, with biocrude production (with transformation of 62.20% with respect to the basic dry biomass) of 28.38 kg/h of biocrude with 3% water following a decantation phase subsequent to the reactor. In addition to obtaining biocrude, a fraction gas is obtained from the thermochemical process (mainly CH$_4$, CO$_2$, and CO), which is burned with a view to obtaining thermal energy for this particular stage.

The final product has a PCI of approximately 9300 kcal/kg, which permits electrical energy of 138 kW to be obtained following combustion in an internal combustion engine with transformation efficiency from thermal energy to electrical energy of 45%. The CO$_2$ resulting from the combustion is reintroduced in the system.

Figure 3:
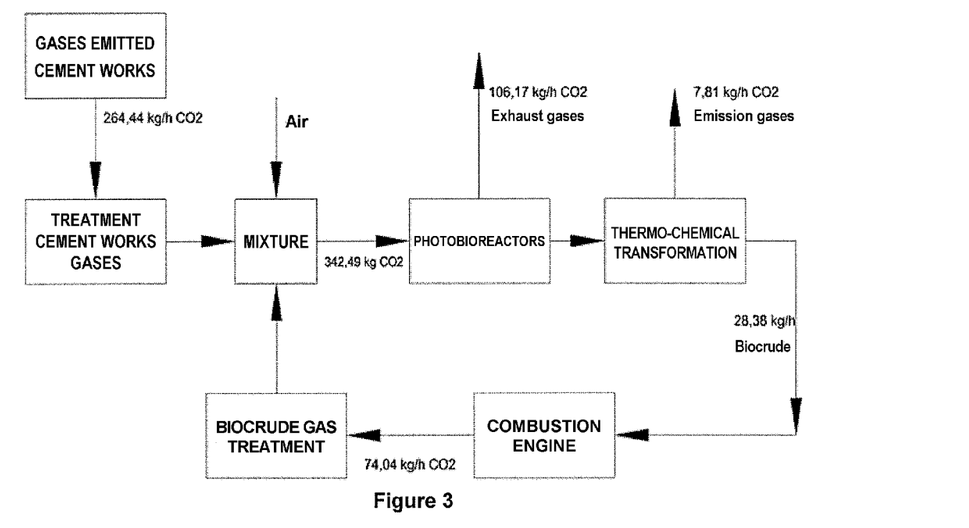
FIG. 3—shows the balance of $CO_2$ emission of example 2 in a procedure for energy conversion of $CO_2$, in accordance with a net negative balance.

FIG. 3 shows the balance of CO$_2$ emissions.

As per the balance, having obtained the electrical energy, following the introduction of 264.44 kg/h of CO$_2$ only 113.98 kg/h of CO$_2$ is emitted, which presupposes a net negative balance of −150.47 kg CO$_2$/h. As a result, in this process not only is CO$_2$ not emitted, but more CO$_2$ is captured than is emitted as per the following balance:

TABLE 6

| | |
|---|---|
| Introduced | 264.44 kg CO$_2$/h |
| Emitted | 113.98 kg CO$_2$/h |
| Balance | −150.47 kg CO$_2$/h |

Example n° 2: Energy Valuation of the CO$_2$

The point of departure is the emission gases resulting from combustion in a cement works with the emissions contained in the following table:

TABLE 7

| Temperature | 150° | C. |
|---|---|---|
| Pressure | 1 | Bar |
| Density | 0.77 | kg/m3 |
| Mass flow | 43,914 | kg/h |
| Specific heat | 0.25 | kcal/kg |
| Volumetric flow | 57,377 | m3/h |
| $CO_2$ | 6% | V |
| $N_2$ | 67.6% | V |
| $O_2$ | 2.1% | V |
| $H_2O$ | 20.7% | V |
| $CH_4$ | 9,000 | Ppm |
| $NO_x$ | 50 | Ppm |
| $SO_x$ | 50 | Ppm |
| CO | 2.69 | Ppm |

Given the characteristics of the gas emitted by the cement works it was considered that the only treatment needed was that of eliminating $SO_x$ and the reduction of temperature. For this purpose an absorption column was installed, in countercurrent with NaOH. It is important to point out that, in this invention procedure in addition to a reduction in the net balance of $CO_2$, a reduction is also obtained in the final concentration of $NO_x$ (95% NO and the remainder $NO_2$) as a result of the dissolution in water of the I NO and $NO_2$ (particularly the latter).

As per this treatment, the following gas is introduced in the photosynthetic reactors (photosynthetic reactors which are continuously agitated and which are made of transparent material to let in light) and which contain a pluripecific micro algae culture (*Nannochloris* sp, *Tetraselmis chuii* and *Isocrisis Galbana*).

TABLE 8

| Temperature | 40° | C. |
|---|---|---|
| Pressure | 1.98 | Bar |
| Density | 2.22 | kg/m3 |
| Mass flow | 38,716 | kg/h |
| Specific heat | 0.24 | kcal/kg |
| Volumetric flow | 17,473 | m3/h |
| $CO_2$ | 7.37% | V |
| $N_2$ | 85.95% | V |
| $O_2$ | 2.95% | V |
| $H_2O$ | 3.69% | V |
| $CH_4$ | 10,502 | ppm |
| $NO_x$ | 23.2 | ppm |
| $SO_2$ | 1 | ppm |
| CO | 0 | ppm |

In accordance with the composition of these gases and the system efficiency in capturing $CO_2$, a production of 4,017 kg/day of biomass is achieved, transformation of which into bio-oil permits 1,607.13 kg/day of biocrude to be obtained in plant with 230 photosynthetic reactors for a total plant volume of 4,020 m³.

In order to obtain this biomass, firstly 1,005 m³ is extracted daily (25% of the culture). This culture having passed to the following centrifugation stage (1$^{st}$ extraction stage) is required to pass through an acidification stage which takes place in a tank, the capacity of which is 1,500 m³. The basis of this acidification stage is as follows:

As a consequence of the continuous bubbling of exhaust gases, the extracted culture has a content of CO2, bicarbonate and carbonate in a high level of dissolution. When this $CO_2$ is allowed to bubble, the pH in the solution tends to rise, displacing the balance towards the formation of carbonates. If a considerable amount of carbonate is formed, it exceeds the point of solubility and begins to precipitate. This precipitation could cause fouling problems and in turn said fouling could cause pollution along with problems in the decanting of water. Therefore, as the mechanical separation (1$^{st}$ separation stage) is not able to process all the extracted volume at one time, during this storage period an acid must be added. Specifically, a solution of HCl (1M) is added in order to ensure that the pH is always below 7.

In this way when the 1005 m³ of culture has been emptied out the water is mechanically separated out from the biomass. This is done through centrifugation, thus obtaining a volume of 36 m³ of concentrated culture, however it is still liquid; the concentration reached being 10% solids.

In addition to the concentrated fraction of 10% solids, an aqueous fraction is obtained (permeated) which amounts to a total of 9,680 m³/per day. This water, due to the fact that it was part of the culture, is charged with $CO_2$, bicarbonate and carbonate. In order to release the water from this charge it is made alkaline with NaOH until it reaches a pH of 9.5 in order to displace the balance towards the formation of carbonate, thus exceeding the limits of the solubility of the carbonate, and causing it to precipitate. In this way CO2 is chemically captured, obtaining a water poor in CO2, bicarbonate and carbonate. The water poor in these elements is introduced into the system again (to the photobioreactors) with a renewed capturing capacity in terms of $CO_2$. If this water is introduced without a previous chemical capture stage, the water's $CO_2$ assimilation capacity would be minimal, as it would be close to saturation.

The concentrate, at 10% solids (36 m³/dia), resulting from centrifugation, passes to a cavitation stage which consists of two steps each at 750 bar; and in this way the cells are fragmented which facilitates the following phase of anaerobic fermentation. This anaerobic fermentation is carried out at 40° C., and in this way the biomass is transformed by the various microbial communities present (anaerobic bacteria) losing O and N in the form of $H_2O$, $CO_2$ y $NH_3$ and becoming enriched in H and C. As the fermentation advances it is noted how the content of N and O begins to drop as the H and C content increases. At the same time methane is generated as a result of the fragmentation of these molecules, energy which is used as a source of thermal energy for the following thermochemical stage. As a result of this fragmentation, of the 4,017 kg of dry biomass which could potentially pass to the next phase, only 2,800 kg/per day pass to the following stage as a result of said fragmentation and decomposition.

Subsequently, following the anaerobic fermentation stage, the resulting product is centrifuged once more, this time until it achieves 23% solids; this product, with a production of 10.7 m³/per day which is already a pasty textured product although one which can be pumped, passes to the following stage of thermochemical transformation. The water resulting from this separation, (19.8 m³ per day), charged with ammonia, is returned to the photobioreactors once more; the ammonia charge serves as a further source of nutrients for the micro-organisms.

The thermo-chemical transformation takes place in a reactor at 300° C. and 15 MPa in a continuous supply process carried out at a rate of 485.24 kg/h of concentrate at 23%, with biocrude being produced (as per a transformation of 60% with respect to the initial dry biomass) at a rate of 1,607.13 kg/per day of biocrude with 7% water following a decantation phase after the reactor.

The final product with an approximate PCI of 8,100 kcal/kg, is burnt in a turbine thus obtaining 284 kW of installed power with a conversion efficiency of thermal energy to electricity of 45%.

Figure 4:
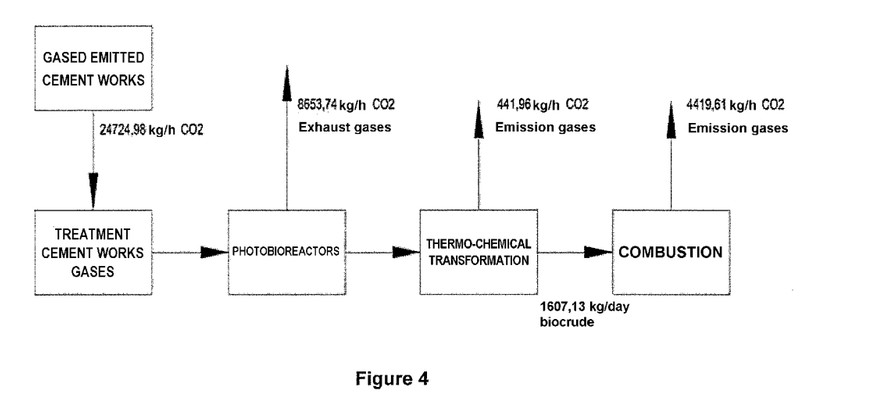
FIG. 4—refers to the balance of $CO_2$ emissions of example 3 in a procedure for energy conversion of $CO_2$, in accordance with a net negative balance.

In accordance with all the foregoing the $CO_2$ balance is shown in FIG. 4.

In accordance with this diagram 24,724.98 kg/per day of $CO_2$ is introduced and 441.96+8,653.74+4,419.61=13,515.31 kg/per day are emitted. Therefore, the net balance is: −11,209.67 kg $CO_2$ per day with more $CO_2$ being captured than emitted.

Example n° 3: Biocrude Based on $CO_2$ from a Cement Works

The point of departure is emission gases resulting from combustion in a cement works, with the emissions indicated in the table below:

TABLE 9

| | |
|---|---|
| Temperature | 170° C. |
| Pressure | 1 bar |
| Density | 0.81 kg/m³ |
| Mass flow | 22,000 kg/h |
| Specific heat | 0.25 kcal/kg |
| Volumetric flow | 27,160.49 m³/h |
| $CO_2$ | 7% V |
| $N_2$ | 66.8% V |
| $O_2$ | 1.9% V |
| $H_2O$ | 17.3% V |
| $CH_4$ | 8,000 ppm |
| NOx | 40 ppm |
| $SO_2$ | 70 ppm |
| CO | 3.69 ppm |

Given the characteristics of the gases it was considered that the only treatment required was the elimination of SOx and a reduction in temperature. For this purpose an absorption column was installed in counter current with NaOH.

Following this treatment the following gases were introduced into the photosynthetic columns:

TABLE 10

| | |
|---|---|
| Temperature | 40° C. |
| Pressure | 1.98 bar |
| Density | 2.22 kg/m3 |
| Mass flow | 19,360 kg/h |
| Temperature | 40° C. |
| Specific heat | 0.24 kcal/kg |
| Volumetric flow | 8,720.72 m³/h |
| $CO_2$ | 7.5% V |
| $N_2$ | 87% V |
| $O_2$ | 2.1% V |
| $H_2O$ | 3.32% V |
| $CH_4$ | 9,600 ppm |
| NOx | 45 ppm |
| $SO_2$ | 1 ppm |
| CO | 0 ppm |

The gases indicated in the above table resulting from the treatment are introduced into the reactors (photosynthetic reactors which are continuously agitated and which are made of transparent material to let in light) and which contain a monospecific microalgae culture (*Isocrisis Galbana*). As a result of this procedure a production of 170 kg/h of biomass is obtained for a 2,041 m³ plant.

In order to obtain this biomass, firstly extraction takes place at the rate of 714 m³ per day (35% of the culture). This extracted culture passes to a decantation tank with a maximum capacity of 1,000 m³, where it is subjected to a stage in which it is separated from the algae (1st phase of extraction) by means of a coagulation-flocculation process. It is coagulated with aluminium, neutralising in this way the charge of microalgae, and it is flocculated with a polyelectrolyte polymer (ZETAG). In this way following 10 minutes of decantation, the biomass is left in the bottom of the tank, obtaining a product with a concentration of 15% solids, which is discharged to the next phase of fermentation.

In addition to the concentrated fraction (15% solids), an aqueous fraction is obtained (leftover in the decantation tank) which amounts to a total volume of 7,026 m³/per day. This water due to the fact that it was part of the culture, is charged with $CO_2$, bicarbonate and carbonate. In order to release water from this load, it is made alkaline with KOH until it reaches pH 9 in order to displace the balance towards the formation of carbonate and in this way exceeds the limit of solubility of the carbonate, causing it to precipitate. In this way the $CO_2$ is captured chemically, obtaining a water poor in $CO_2$, bicarbonate and carbonate. The water which is poor in these elements is introduced in the system again (to the photo reactors) with a capacity for renewed capture in respect of $CO_2$. If this water were introduced without proceeding to a prior phase of chemical capture, the water's capacity of CO2 assimilation would be minimal, as it would be close to saturation.

The concentrate, which is 15% solids (11.56 m³/per day), resulting from centrifugation, passes to an anaerobic fermentation phase at 33° C. During the anaerobic fermentation the biomass is transformed by the different microbial communities present (anaerobic bacteria) losing O and N in the form of $H_2O$, $CO_2$ and $NH_3$ and becoming enriched in H and C. As the fermentation progresses, it is possible to note how the N and O content drops as the H and C increases. At the same time methane is generated as a result of the fragmentation of these molecules, which is used as a source of thermal energy for the subsequent thermochemical stage. In accordance with this fragmentation of 2,040.65 kg of dry biomass per day which could potentially pass to the next stage, only 1,360 kg per day pass to the following phase as a result of said fragmentation and decomposition.

Table 9 below shows the development of the C, N, O and H in accordance with the fermentation process:

TABLE 11

| | Prior to fermentation (%) | Following fermentation (%) |
|---|---|---|
| C | 50.3 | 60 |
| N | 7.3 | 2 |
| O | 26.82 | 17.7 |
| H | 7.58 | 12.3 |

Subsequently, following the anaerobic fermentation stage the resulting product is subjected to a pressed filtration process in order to increase the solid content. The cake resulting from this phase is a wet product with a 30% concentrate of solids. This product in product ion of 4,534,77 kg per day has a pasty texture, however, it can be pumped and passes to the next stage of thermochemical transformation. The resulting clearer water (11.47 m³ per day), is charged with ammonia and is returned to the photoreactors once more; the ammonia charge serves as a further provision of nutrients for the micro-organisms.

The thermochemical transformation takes place in a reactor at 320° C. and 20 MPa in a continuous process, supplied at a rate of 189 kg/h, with bio-oil production (in accordance with a transformation of 52% with respect to the basic dry biomass) of 29.47 kg/h with 5% water following a phase of decantation subsequent to the reactor.

Figure 5:
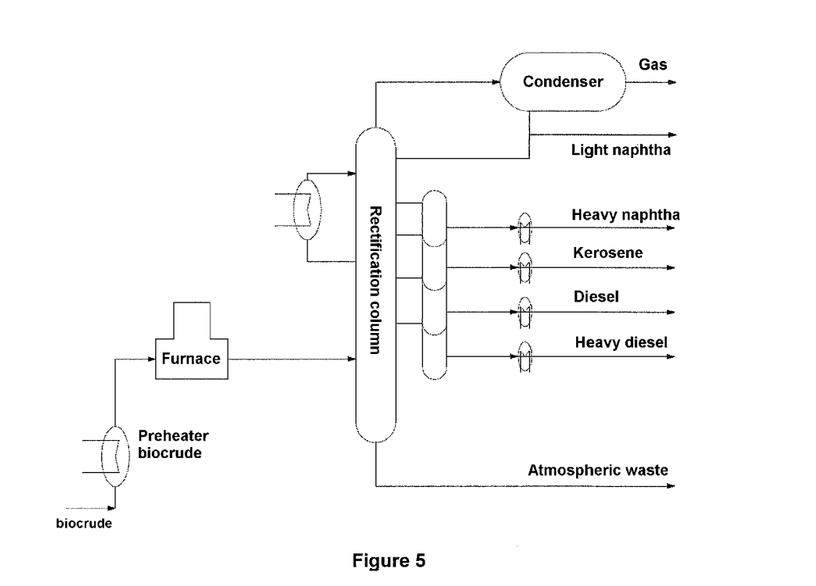
FIG. 5—shows the division of the biocrude into different fractions.

The final product has a PCI of approximately 8,400 kcal/kg, which, following a stage of water removal through vacuum evaporation, is refined in order to obtain different fractions as shown in the following figure with the process described as follows: the biocrude is preheated, subsequently passing to a furnace where the biocrude is partially vaporised. Subsequently it passes to the distillation or rectification column and is separated into different fractions based on the boiling temperature. The percentages are as follows:

5.6%→Gases
11%→light naphtha
23.8%→heavy naphtha
18%→Kerosene
29.6%→Diesel
12%→Heavy gas-oil.

The invention claimed is:

1. Procedure for obtaining a biocrude from a gas comprising $CO_2$, procedure which comprises the steps of:
   a. supply of the gas which comprises $CO_2$ to a reactor containing a culture which comprises at least one species of microalga which is capable of photosynthesis;
   b. photosynthesis carried out by the species of microalga using the $CO_2$ supplied to produce a biomass;
   c. anaerobic fermentation of the biomass obtained;
   d. thermochemical decomposition of the biomass fermented at a pressure between 0 and 20 MPa and a temperature between 200 and 420° C. in order to obtain a biocrude mixed with water and gases, and
   e. separation of the biocrude obtained,
   characterised in that following the photosynthesis stage, between 5 and 100% of the culture is removed from the reactor which is subsequently separated into a solid fraction which contains biomass, which solid fraction will subsequently be subjected to the stage of anaerobic fermentation, and a liquid fraction containing carbonates and/or bicarbonates, which are separated from the liquid fraction, and which liquid fraction is returned at least partially to the reactor devoid of carbonates and bicarbonates.

2. Procedure according to claim 1, in which in the step of at least partial removal from the reactor, between 5 and 50% of culture is removed.

3. Procedure according to claim 2, in which in the step of at least partial removal from the reactor, approximately 10% of culture is removed.

4. Procedure according to claim 1, wherein prior to the step of supply of a gas comprising $CO_2$ to the reactor, said gas is pre-treated by at least one of the following treatments: a) substantial elimination of $SO_x$, $NO_x$, (b) substantial elimination of humidity and (c) adaptation of the gas temperature to between 30 and 40° C.

5. Procedure according to claim 1, wherein the photosynthesis step is carried out in a turbulent regime and exposed to natural and/or artificial light.

6. Procedure according to claim 1, wherein following the step of at least partial removal of the culture from the reactor, the removed culture is acidified to a pH between 3.5 and 8.

7. Procedure according to claim 6, wherein the removed culture is acidified to a pH between 6 and 8.

8. Procedure according to claim 6, wherein the acidification is carried out by adding to the culture at least one acidifying agent selected from the group consisting of $CO_2$, mixture of $CO_2$ and air, strong or weak acids or any combination thereof.

9. Procedure according to claim 8, wherein the acidification is carried out by adding to the culture a mixture of $CO_2$ and air.

10. Procedure according to claim 1, wherein following the step of at least partial removal of the culture from the reactor, separation of the solid fraction which contains biomass and the liquid fraction which contains carbonates and/or bicarbonates is carried out through at least one technique selected from the group consisting of filtration, centrifugation, flocculation, electro coagulation, ultrasound, evaporation, decantation or any combination thereof.

11. Procedure according to claim 1, wherein the separation of carbonates and/or bicarbonates from the liquid fraction resulting from the at least partial removal of the culture from the reactor is carried out through precipitation of the corresponding carbonated salts deriving from the addition of at least one alkali.

12. Procedure according to claim 1, wherein the anaerobic fermentation step comprises anaerobic fermentation of a biomass in which the concentration of solids is from 1 to 50% and which is carried out at a temperature between 10 and 165° C.

13. Procedure according to claim 12, wherein the biomass has a 5 to 12% concentration of solids and the anaerobic fermentation is carried out at a temperature between 30 and 75° C.

14. Procedure according to claim 13, wherein the anaerobic fermentation is carried out at a temperature of approximately 38° C.

15. Procedure according to claim 1, wherein previously or subsequent to the anaerobic fermentation step, a sub step of homogenisation or cavitation of the biomass is carried out during which it is subjected to pressure between 1 bar and 2,500 bar.

16. Procedure according to claim 15, in which the biomass is subjected to pressure between 250 and 1,200 bar.

17. Procedure according to claim 15, which is repeated between 1 and 5 times.

18. Procedure according to claim 1, wherein the thermochemical decomposition step of the fermented biomass is carried out by heating the mass to a temperature between 240 to 340° C. and a pressure of 10 to 20 MPa.

19. Procedure according to claim 1, wherein following the step of anaerobic fermentation and prior to the step of thermo-chemical decomposition, an aqueous fraction containing ammonium salts is separated from the biomass resulting from the anaerobic fermentation, which aqueous fraction is then returned to the reactor again.

20. Procedure according to claim 1, wherein the species of micro alga which carries out the photosynthesis is selected from the group consisting of Chlorophyceae, Bacillariophyceae, Dinophyceae, Cryptophyceae, Chrysophyceae, Haptophyceae, Prasinophyceae, Raphidophyceae, Eustigmatophyceae, or any combination thereof.

21. Procedure according to claim 1, wherein the gas which comprises $CO_2$ and which is supplied to the reactor proceeds in an exogenous way from the atmosphere or from any industry and/or in an endogenous way from the gases generated in the actual procedure, in any combination thereof.

22. Procedure according to claim 21, in which the exogenous component of the gas containing $CO_2$ proceeds from a cement works or similar industry.

23. Procedure according to claim 1, wherein the gas comprising $CO_2$ further comprises other greenhouse gases selected from the group consisting of $NO_x$, $CH_4$ and mixtures thereof.

24. Procedure according to claim 1, which includes a final step of refining of the biocrude obtained.

* * * * *